(12) United States Patent
Knight et al.

(10) Patent No.: US 10,952,593 B2
(45) Date of Patent: Mar. 23, 2021

(54) BRONCHOSCOPE ADAPTER

(71) Applicant: COVIDIEN LP, Mansfield, MA (US)

(72) Inventors: Trevor C. Knight, Minnetonka, MN (US); Seamus P. Maguire, Athlone (IE)

(73) Assignee: Covidien LP, Mansfield, MA (US)

( * ) Notice: Subject to any disclaimer, the term of this patent is extended or adjusted under 35 U.S.C. 154(b) by 513 days.

(21) Appl. No.: 14/664,548

(22) Filed: Mar. 20, 2015

(65) Prior Publication Data
US 2015/0351613 A1 Dec. 10, 2015

Related U.S. Application Data

(60) Provisional application No. 62/010,234, filed on Jun. 10, 2014.

(51) Int. Cl.
A61B 1/00 (2006.01)
A61M 16/04 (2006.01)
A61M 39/10 (2006.01)
A61B 1/267 (2006.01)
A61M 16/08 (2006.01)

(52) U.S. Cl.
CPC ........ *A61B 1/00128* (2013.01); *A61B 1/2676* (2013.01); *A61M 16/04* (2013.01); *A61M 16/0463* (2013.01); *A61M 16/0488* (2013.01); *A61M 16/0816* (2013.01); *A61M 39/105* (2013.01); *A61M 39/1011* (2013.01); *A61B 1/00154* (2013.01); *A61M 2039/1033* (2013.01); *A61M 2039/1044* (2013.01)

(58) Field of Classification Search
CPC .............. A61B 1/2676; A61B 1/00147; A61B 1/00137; A61B 1/00128; A61B 1/0014; A61B 1/00154; A61M 16/0497; A61M 16/0427; A61M 16/0434; A61M 16/0488
USPC ......................................................... 600/125
See application file for complete search history.

(56) References Cited

U.S. PATENT DOCUMENTS 1,576,781 A 3/1926 Phillips
1,735,726 A 11/1929 Bornhardt
(Continued)

FOREIGN PATENT DOCUMENTS

CA 964149 3/1975
CN 103111009 A 5/2013
(Continued)

OTHER PUBLICATIONS

European Search Report dated Sep. 9, 2015, issued in European Application No. 15171166.
(Continued)

*Primary Examiner* — Alexandra L Newton

(57) ABSTRACT

A bronchoscope locking mechanism includes a clamping member and a nut. The clamping member includes a threaded portion and a clamping surface that defines a compressible channel. The compressible channel is configured for communication with a tracheal tube. The nut has an inner threaded surface configured to cooperate with the threaded portion of the clamping member. The compressible channel is compressed from a first position defining a first diameter to a second position defining a second diameter when the nut is advanced over the threaded portion. The second diameter is smaller than the first diameter.

11 Claims, 10 Drawing Sheets

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,191,652 A | 6/1965 | Benson et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,024,997 A | 5/1977 | Kolpin |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,447,462 A | 5/1984 | Tafuri et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,559,046 A | 12/1985 | Groshong et al. |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,685,583 A | 8/1987 | Noon |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |

(56) References Cited

U.S. PATENT DOCUMENTS

| | | | |
|---|---|---|---|
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,021,888 A | 6/1991 | Kondou et al. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,186 A | 10/1991 | Yamamoto et al. |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,158 A | 4/1992 | Meyer |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,171,245 A | 12/1992 | Cezana |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,250,069 A | 10/1993 | Nobuyoshi et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,320,249 A | 6/1994 | Strech |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,366,446 A * | 11/1994 | Tal ................. A61B 17/34 |
| | | 604/180 |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |

(56) References Cited

U.S. PATENT DOCUMENTS

| | | |
|---|---|---|
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz et al. |
| 5,515,641 A | 5/1996 | D'Alessandro |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-Haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,582,575 A | 12/1996 | Heckele et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,707 A | 5/1998 | Miyagawa et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kailas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,842,984 A | 12/1998 | Avitall |

(56) References Cited

U.S. PATENT DOCUMENTS

| | | |
|---|---|---|
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,134,003 A | 10/2000 | Tearney et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,286,798 B1 | 9/2001 | Chun |
| 6,298,262 B1 | 10/2001 | Franck et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,343,728 B1 | 2/2002 | Carbone |
| 6,345,112 B1 | 2/2002 | Summers et al. |
| 6,351,659 B1 | 2/2002 | Vilsmeier |
| 6,355,027 B1 | 3/2002 | Le et al. |
| 6,366,799 B1 | 4/2002 | Acker et al. |
| 6,368,316 B1 | 4/2002 | Jansen et al. |
| 6,373,240 B1 | 4/2002 | Govari |
| 6,381,485 B1 | 4/2002 | Hunter et al. |
| 6,381,490 B1 | 4/2002 | Ostrovsky |
| 6,422,994 B1 | 7/2002 | Kaneko et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,485,413 B1 | 11/2002 | Boppart et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,547,722 B1 | 4/2003 | Higuma et al. |
| 6,551,325 B2 | 4/2003 | Neubauer et al. |

(56) References Cited

U.S. PATENT DOCUMENTS

| | | |
|---|---|---|
| 6,579,277 B1 | 6/2003 | Rabiner et al. |
| 6,580,938 B1 | 6/2003 | Acker |
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,612,485 B2 | 9/2003 | Lackner et al. |
| 6,618,612 B1 | 9/2003 | Acker et al. |
| 6,626,339 B2 | 9/2003 | Gates et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,706,041 B1 | 3/2004 | Costantino |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |
| 6,887,236 B2 | 5/2005 | Gilboa |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Yokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 8,663,088 B2 | 3/2014 | Greenburg et al. |
| 2001/0004676 A1 | 6/2001 | Ouchi |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0026097 A1 | 2/2002 | Akiba |
| 2002/0067408 A1 | 6/2002 | Adair et al. |
| 2002/0072712 A1 | 6/2002 | Nool et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0028096 A1 | 2/2003 | Niwa et al. |
| 2003/0040657 A1 | 2/2003 | Yamaya et al. |
| 2003/0074011 A1 | 4/2003 | Gilboa et al. |
| 2003/0086599 A1 | 5/2003 | Armato et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller |
| 2005/0011786 A1 | 1/2005 | Wood et al. |
| 2005/0033149 A1 | 2/2005 | Strommer et al. |
| 2005/0059890 A1 | 3/2005 | Deal et al. |
| 2005/0080342 A1 | 4/2005 | Gilreath et al. |
| 2005/0085715 A1 | 4/2005 | Dukesherer et al. |
| 2005/0090818 A1 | 4/2005 | Pike et al. |
| 2005/0107688 A1 | 5/2005 | Strommer |
| 2005/0119527 A1 | 6/2005 | Banik et al. |
| 2005/0182292 A1 | 8/2005 | Suzuki |
| 2005/0182295 A1 | 8/2005 | Soper et al. |
| 2005/0197566 A1 | 9/2005 | Strommer et al. |
| 2005/0229934 A1 | 10/2005 | Willeford |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon et al. |
| 2006/0149134 A1 | 7/2006 | Soper et al. |
| 2006/0184016 A1 | 8/2006 | Glossop |
| 2007/0163597 A1 | 7/2007 | Mikkaichi et al. |
| 2007/0167682 A1* | 7/2007 | Goldfarb ............ A61B 1/00135 600/114 |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0225559 A1 | 9/2007 | Clerc et al. |
| 2007/0265639 A1 | 11/2007 | Danek et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |

(56) References Cited

U.S. PATENT DOCUMENTS

| | | |
|---|---|---|
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |
| 2009/0234223 A1 | 9/2009 | Onoda et al. |
| 2009/0318797 A1 | 12/2009 | Hadani |
| 2010/0016757 A1 | 1/2010 | Greenburg et al. |
| 2010/0024818 A1 | 2/2010 | Stenzler et al. |
| 2010/0198007 A1 | 8/2010 | Greenburg et al. |
| 2011/0023875 A1 | 2/2011 | Ledwith |
| 2012/0253119 A1 | 10/2012 | Meloul |
| 2013/0023729 A1* | 1/2013 | Vazales ............... A61B 1/0669 600/104 |
| 2013/0104884 A1 | 5/2013 | Vazales et al. |
| 2014/0194907 A1* | 7/2014 | Bonutti ............. A61B 17/8866 606/151 |

FOREIGN PATENT DOCUMENTS

| | | |
|---|---|---|
| DE | 3042343 A1 | 6/1982 |
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19705331 A1 | 8/1997 |
| DE | 19610984 A1 | 9/1997 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0651968 A1 | 5/1995 |
| EP | 0655138 A1 | 5/1995 |
| EP | 0796633 A1 | 9/1997 |
| EP | 0857461 A2 | 8/1998 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1255113 A1 | 11/2002 |
| EP | 1543765 A1 | 6/2005 |
| EP | 1667749 A2 | 6/2006 |
| EP | 2096523 A1 | 9/2009 |
| EP | 2574271 A1 | 4/2013 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | H04261666 A | 9/1992 |
| JP | 06-125869 A | 5/1994 |
| JP | 06194639 A | 7/1994 |
| JP | 07-043619 A | 2/1995 |
| JP | 09-253038 A | 9/1997 |
| JP | 10-197807 A | 7/1998 |
| JP | 2000-075218 A | 3/2000 |
| JP | 2000-279379 A | 10/2000 |
| JP | 2001-231743 A | 8/2001 |
| JP | 2001-275942 A | 10/2001 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 96/11624 A2 | 4/1996 |
| WO | 96/32059 A1 | 10/1996 |
| WO | 97/29682 A1 | 8/1997 |
| WO | 97/29684 A1 | 8/1997 |
| WO | 97/36192 A1 | 10/1997 |
| WO | 97/49453 A1 | 12/1997 |
| WO | 98/08554 A1 | 3/1998 |
| WO | 98/38908 A1 | 9/1998 |
| WO | 99/15097 A2 | 4/1999 |
| WO | 99/21498 A1 | 5/1999 |
| WO | 99/23956 A1 | 5/1999 |
| WO | 99/26549 A1 | 6/1999 |
| WO | 99/27839 A2 | 6/1999 |
| WO | 99/29253 A1 | 6/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 99/60939 A1 | 12/1999 |
| WO | 00/06701 A1 | 2/2000 |
| WO | 00/14056 A1 | 3/2000 |
| WO | 00/16684 A1 | 3/2000 |
| WO | 00/35531 A1 | 6/2000 |
| WO | 01/19235 A1 | 3/2001 |
| WO | 01/30437 A1 | 5/2001 |
| WO | 01/67035 A1 | 9/2001 |
| WO | 01/87136 A2 | 11/2001 |
| WO | 01/87398 A2 | 11/2001 |
| WO | 01/91842 A1 | 12/2001 |
| WO | 02/24054 A2 | 3/2002 |
| WO | 02/064011 A2 | 8/2002 |
| WO | 02/070047 A1 | 9/2002 |
| WO | 03/086498 A2 | 10/2003 |
| WO | 2004/023986 A1 | 3/2004 |
| WO | 2005025635 A2 | 3/2005 |
| WO | 2005046785 A1 | 5/2005 |
| WO | 2005074380 A2 | 8/2005 |
| WO | 2006/116597 A2 | 11/2006 |
| WO | 2007109418 A2 | 9/2007 |
| WO | 2009040657 A2 | 4/2009 |
| WO | 2010022363 A1 | 2/2010 |
| WO | 2014184636 A2 | 11/2014 |

OTHER PUBLICATIONS

European Search Report dated Mar. 7, 2017, issued in EP Application No. 15171166.
Chinese Office Action dated Dec. 1, 2017, issued in CN Application No. 201510294249.
Chinese Office Action dated Jul. 6, 2018 in CN Appln. No. 201510294249.

(56) References Cited

OTHER PUBLICATIONS

Chinese Office Action dated Jul. 15, 2019 issued in corresponding CN Appln. No. 201510294249.2.

* cited by examiner

BRONCHOSCOPE ADAPTER

CROSS REFERENCE TO RELATED APPLICATION

The present application claims the benefit of and priority to U.S. Provisional Application Ser. No. 62/010,234, filed on Jun. 10, 2014, the entire contents of which are incorporated herein by reference.

BACKGROUND

1. Technical Field

The present disclosure relates to bronchoscopy and, more specifically, to adapters for connecting, securing, and sealing a bronchoscope.

2. Discussion of Related Art

Patients being ventilated may have their airway secured by an endotracheal tube. The endotracheal tube is usually made from rubber or plastic and inserted either through the natural upper airways, i.e. mouth or nose, pharynx, and larynx, or by surgical access to the trachea, i.e. tracheostomy. The endotracheal tube may be equipped with an inflatable cuff around its tracheal end, which seals the trachea and thus allows positive pressure ventilation and protects the airway from contamination by foreign matter. Generally, the end of the tube distal to the patient is either coupled to a ventilator via a tubing system or open to ambient air via a check valve at its outlet.

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to diagnostic (e.g., biopsy tools) and therapeutic (e.g., laser, cryogenic, radio frequency, or microwave tissue treatment probes) instruments. The distal tip of a bronchoscope is steerable. Rotating a lever placed at the handle of the bronchoscope actuates a steering mechanism that deflects the tip in one or more directions.

Bronchoscopies are performed by pulmonologists, also known as bronchoscopists, and are used routinely in the diagnosis and treatment of conditions such as lung cancer, airway stenosis, and emphysema. Bronchoscopies are typically performed by a staff of at least two persons: the bronchoscopist and at least one assistant, usually a nurse. During a typical procedure, the bronchoscopist holds the bronchoscope handle with one hand and the bronchoscope tube with the other hand. The bronchoscopist manipulates the distal tip of the bronchoscope inside the lung by rotating a deflection lever and by pushing and pulling the tube. Once the tip is brought to a target, an instrument can be inserted into the working channel to perform a diagnostic or therapeutic procedure.

During insertion and operation of the instruments, the distal tip of the bronchoscope should be held steady at the target. Two hands are needed to secure the bronchoscope in place and one to two more hands are needed for inserting and actuating the instrument. Generally, the bronchoscopist releases the bronchoscope to insert and actuate the instrument. Performing a procedure that requires two people is generally more expensive and the potential for error is increased. Hence, it is desirable to modify a procedure so that it may be performed with one or two hands, if possible.

Additionally, because all of the instruments used with a bronchoscope are necessarily long and slender, the instruments do not retain shape when unsupported. Thus, inserting an instrument into a bronchoscope can be difficult or impossible to do quickly with one hand. While this problem can be addressed easily by holding the end of the sheath in one hand and the instrument in another, this would again require additional free hands during performance of the procedure.

Accordingly, there is a need for an adaptor for use with a bronchoscope that would facilitate operation of a bronchoscope and associated tools by a single practitioner. It would also be advantageous to provide an adapter for the connection port of the working channel of a bronchoscope that performs both sealing and instrument-locking functions without requiring replacement of an attachment during the procedure.

SUMMARY

In an aspect of the present disclosure, a bronchoscope locking mechanism includes a clamping member and a nut. The clamping member includes a threaded portion and a clamping surface. The clamping surface defines a compressible channel configured for communication with a tracheal tube. The nut includes an inner threaded surface and an outer surface. The inner threaded surface is configured to cooperate with the threaded portion of the clamping member. In a first position of the compressible channel, the compressible channel defines a first diameter and in a second position of the compressible channel, the compressible channel defines a second diameter smaller than the first diameter. As the nut is advanced over the threaded portion, the nut interferes with the clamping member such that the compressible channel is moved from the first position towards the second position. The clamping member may include two or more lobes. The clamping member may include a cantilevered member having the clamping surface.

In some embodiments, the nut may be advanced proximally over the threaded portion to transition the compressible channel from the first position to the second position. In other embodiments, the nut is advanced distally over the threaded portion to transition the compressible channel from the first position to the second position.

In certain embodiments, the outer surface of the nut is configured to enhance tactile feel. The outer surface of the nut may include rounded protrusions, petal-shaped protrusions, star-shaped protrusion, wings, or knurling to enhance the tactile feel.

In some aspects of the present disclosure, a tracheal tube adaptor assembly includes a bronchoscope, an elongated tube having a proximal portion and a distal portion, and a locking mechanism. The locking mechanism is positioned proximal of the elongated tube and defines a longitudinal axis. The locking mechanism includes a clamping member and a nut. The clamping member defines a compressible channel axially aligned with the proximal portion of the elongated tube. The nut includes an inner threaded surface and an outer surface. The inner threaded surface is configured to cooperate with the threaded portion of the clamping member. The compressible channel has a first position defining a first diameter and a second position defining a second diameter. The bronchoscope is free to slide within the compressible channel when the compressible channel is in the first position and the bronchoscope is longitudinally fixed within the compressible channel when the compressible channel is in the second position. As the nut is advanced over the threaded portion, the nut interferes with the clamping member such that the compressible channel is moved from the first position towards the second position. The clamping surface of the locking mechanism may form a seal with a bronchoscope.

In some embodiments, the locking mechanism is positioned about the proximal portion of the elongated tube. In certain embodiments, the elongated tube has a proximal flange positioned near a proximal end of the elongated tube.

In some embodiments, the tracheal tube assembly further includes an elbow portion, a first connector, and a second connector. The elbow portion includes a sidewall opening and is positioned distal to the locking mechanism. The second connector is positioned distal to the elbow portion. The elbow portion and the second connector are axially aligned with the locking mechanism. The second connector is positioned between the locking mechanism and the elongated tube. The first connector includes an elongated body. An end of the elongated body is coupled to the sidewall opening of the elbow portion. The elbow portion may define a first passage and the second connector may define a second passage in fluid communication with the first passage. The elongated body of the first connector may define a first lumen in fluid communication with the first and second passages through the sidewall opening of the elbow portion. The elongated body of the first connector may further define a second lumen adjacent the first lumen. The second lumen may be in fluid communication with the first and second passages through the sidewall opening of the elbow portion. The first lumen may be configured to permit fluid to flow into the first and second passages and to inhibit fluid from flowing from the first and second passages. The second lumen is configured to permit fluid to flow from the first and second passages and inhibit fluid from flowing into the first and second passages.

In aspects of the present disclosure, a method for securing a bronchoscope includes inserting a bronchoscope into a compressible channel of a locking mechanism and securing the bronchoscope in the locking mechanism by advancing a nut over a threaded portion of the locking mechanism. The nut compresses a clamping surface to reduce a diameter of the compressible channel. In embodiments, the method further includes inserting an instrument through the bronchoscope after the bronchoscope is secured in the locking mechanism.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
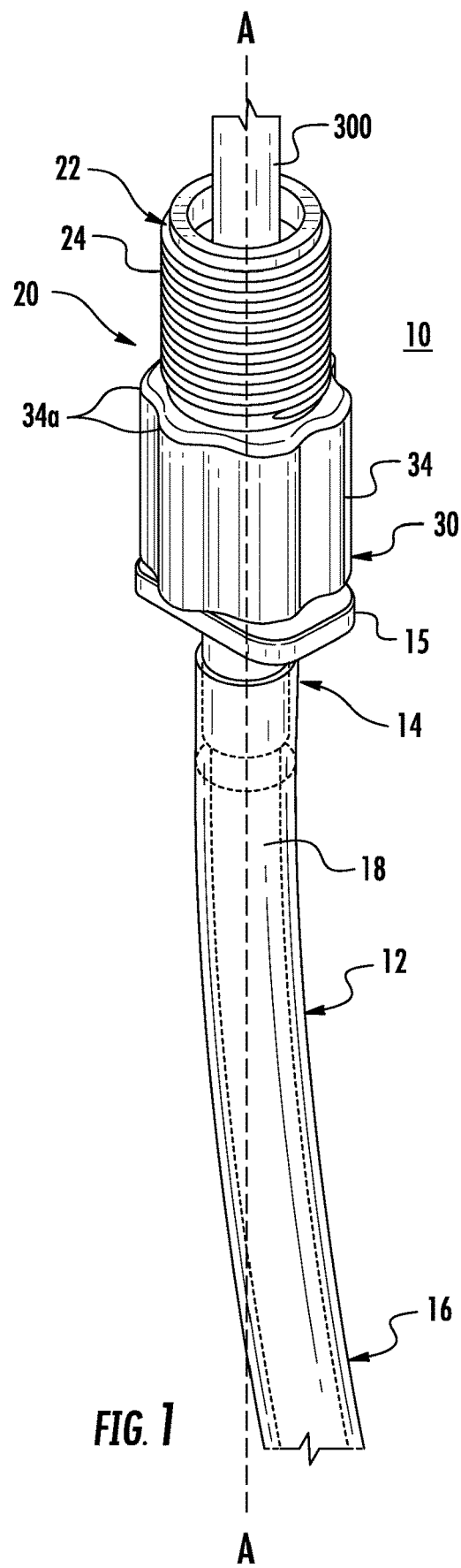
FIG. 1 is a perspective view of a tracheal tube assembly provided in accordance with the present disclosure with the channel in an uncompressed condition.

Embodiments of the present disclosure are now described in detail with reference to the drawings in which like reference numerals designate identical or corresponding elements in each of the several views. As used herein, the term "clinician" refers to a bronchoscopist, a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician.

Referring now to FIG. 1, a trachael tube assembly 10 provided in accordance with the present disclosure incorporating a tracheal or elongated tube 12 and a bronchoscope locking mechanism 20. The elongated tube 12 has a proximal portion 14 and a distal portion 16 defining a lumen 18 therethrough. The proximal portion 14 couples to a connector 15. The bronchoscope locking mechanism 20 is disposed over the outer surface of the connector 15 in a sealing relationship. The bronchoscope locking mechanism 20 is fixed relative to the connector 15. The bronchoscope locking mechanism 20 defines a longitudinal axis "A-A".

Figure 2:
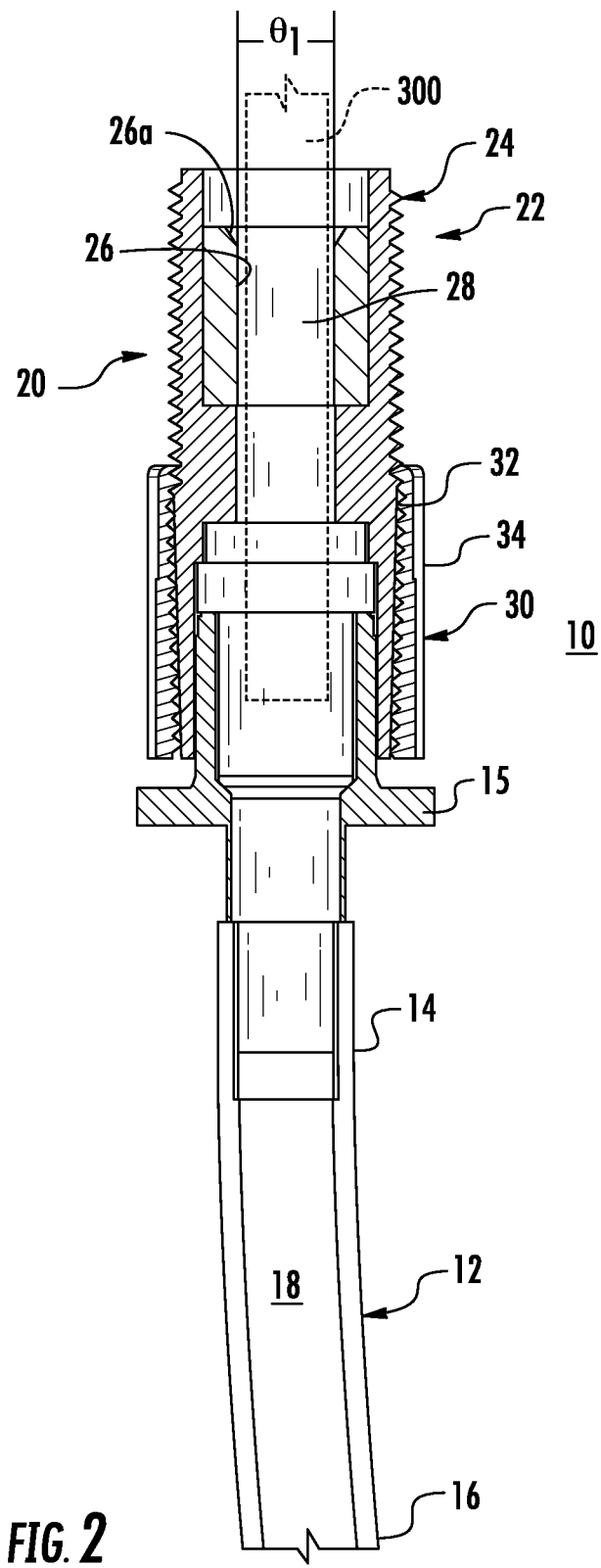
FIG. 2 is a cross-sectional view of the tracheal tube assembly of FIG. 1 taken along the longitudinal axis.

With additional reference to FIG. 2, the locking mechanism 20 includes a clamping member 22 and a nut 30. The locking mechanism 20 can be positioned near a proximal end of the proximal portion 14. The clamping member 22 includes a threaded portion 24, a clamping surface 26, and a compressible channel 28. The clamping surface 26 is positioned about the longitudinal axis "A-A" to define a compressible channel 28. In embodiments, the clamping surface 26 includes an angled guide 26a configured to urge a distal end of a bronchoscope 300 into channel 28 when bronchoscope 300 is inserted into the lumen 18.

The nut 30 includes a threaded inner surface 32 and an outer surface 34. The threaded inner surface 32 of the nut 30 is configured to engage threads of the threaded body 24. The outer surface 34 of the nut 30 can shaped to enhance the tactile feel and/or engagement by the hand and/or finger of a clinician. As shown in FIG. 1, the outer surface 34 includes six rounded protrusions 34a radially positioned about the longitudinal axis "A-A". The outer surface 34 can be knurled, petal-shaped, star-shaped, include wings, or have any other shape or feature to enhance the tactile feel or ease engagement by a clinician to rotate the nut 30 about the threaded body 24.

Figure 3:
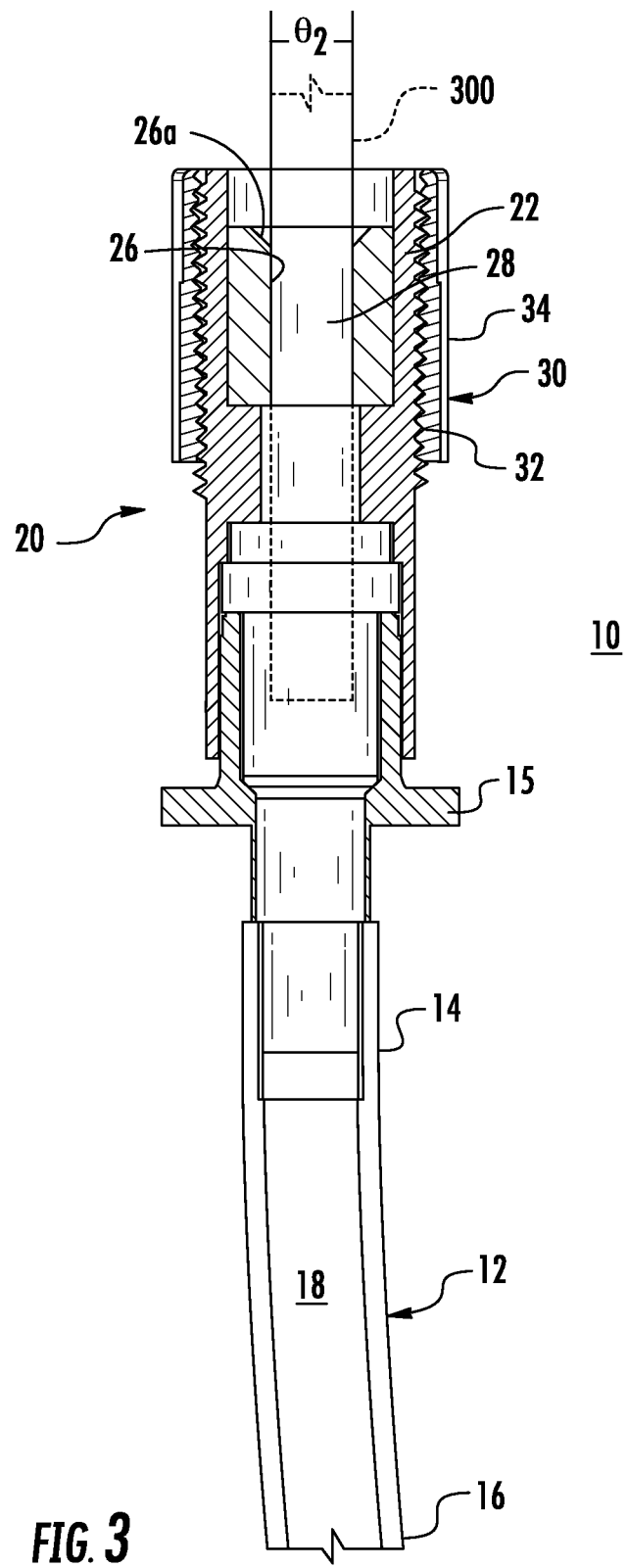
FIG. 3 is a cross-sectional view of the tracheal tube assembly of FIG. 1 taken along the longitudinal axis with the channel in a compressed condition.

Referring now to FIGS. 2 and 3, the threaded inner surface 32 of the nut 30 is tapered such that as the nut 30 is advanced over the threaded portion 24, the threaded inner surface 32 of the nut 30 interferes with the threaded portion 24 to compress the clamping surface 26 inwards. The diameter of channel 28 is reduced as the clamping surface 26 is compressed inwards. The channel 28 has an uncompressed or first diameter $\theta_1$, before the nut 30 interferes with the threaded portion 24, and a compressed or second diameter $\theta_2$, after the nut 30 is in an advanced position over the threaded portion 24 and interferes with the threaded portion 24. It can be appreciated that as the nut 30 is advanced over the threaded portion 24, the diameter of channel 28 transitions from the first diameter $\theta_1$ to the second diameter $\theta_2$, the second diameter $\theta_2$ being smaller than the first diameter $\theta_1$. For example, the channel 28 can be configured to accept a bronchoscope 300 having an outer diameter of 5.7 mm. In this example, a first diameter $\theta_1$ of channel 28 is greater than 5.7 mm, allowing the bronchoscope 300 to pass freely through channel 28, and a second diameter $\theta_2$ of channel 28 that is less than 5.7 mm such that the clamping surface 26 engages the bronchoscope 300 to lock the bronchoscope 300 in a fixed longitudinal position. The clamping surface 26 can be constructed of a compliant material that deforms or compresses when it contacts the bronchoscope 300. In some embodiments, the bronchoscope 300 can rotate when engaged by the clamping surface 26. In certain embodiments, the bronchoscope 300 is rotatably and longitudinally fixed when engaged by the clamping surface 26. In particular embodiments, the engagement of the clamping surface 26 with the bronchoscope 300 is adjustable as the nut 30 advances over the threaded portion 24 to first longitudinally fix the bronchoscope 300 then to rotatably fix the bronchoscope 300 relative to the locking mechanism 20.

Figure 2A:
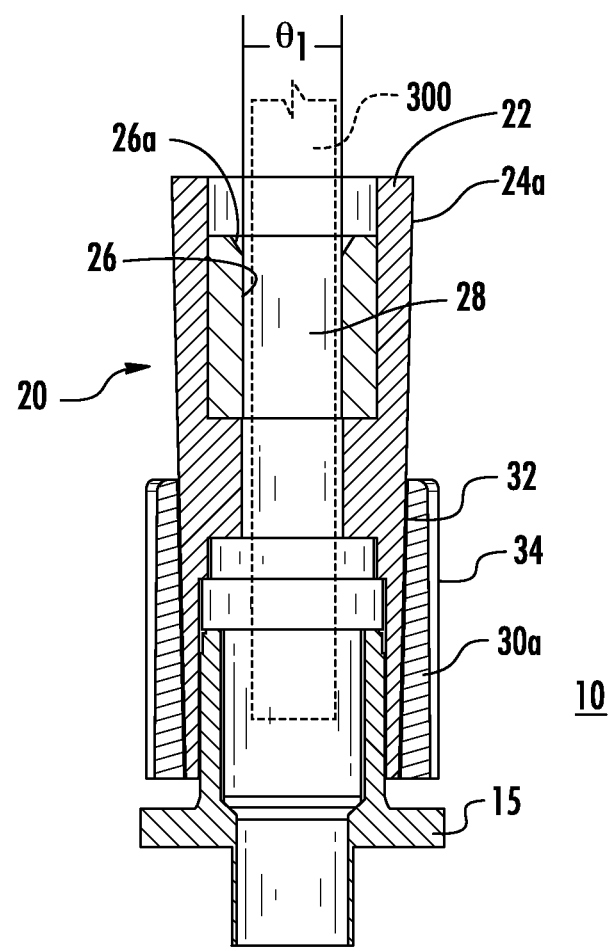
FIGS. 2A and 2B are side cross-sectional views of embodiments of other tracheal tube assemblies in accordance with the present disclosure.

In accordance with another embodiment instead of a threaded portion 24, a tapered compressible portion 24a of the clamping member 22, shown in FIG. 2A, mates an oppositely tapered slide 30a. The slide 30a is advanced (moved proximally) over the tapered compressible portion 24a to compress the clamping member 22 to fix the bronchoscope 300 within the locking mechanism 20 and retracted (moved distally) to release the compression of the clamping member 22 on the bronchoscope 300. In some embodiments, the tapered slide 30a may be integrally formed with the tapered compressible portion 24a of the clamping member 22.

Figure 2B:
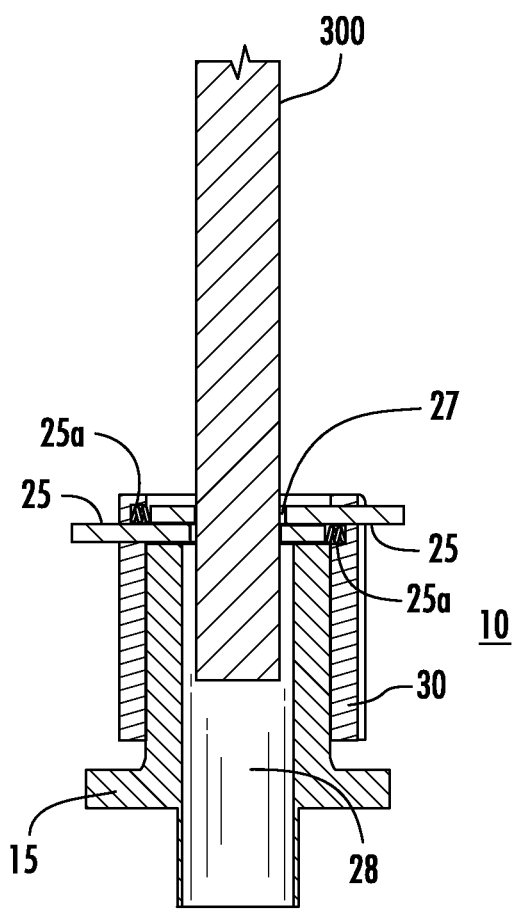

Alternatively, as shown in FIG. 2B the locking mechanism 20 may include two or more spring loaded plates 25 orientated orthogonal to the longitudinal axis. Each plate 25 includes a central passage 27 positioned over the channel 28 when the plates 25 are in an unclamped position. The first plate 25, and particularly the central passage 27 is biased to a clamped position offset in a first direction transverse to the longitudinal axis and the second plate 25, and particularly the central passage 27 is biased to a clamped position offset in a second direction transverse to the longitudinal axis, the second direction opposite the first direction. To insert a bronchoscope 300 the first and second plates 25 are moved in opposite directions of their offset to the channel 28 to the unclamped position such that the central passages 27 of each plate 25 are aligned with the channel 28. When the bronchoscope is passed through the central passages of the plates, the plates 25 are released and biased by spring action (e.g., springs 25a) such that each plate 25 moves towards its clamped position to fix the bronchoscope 300 within the channel 28.

Figure 4:
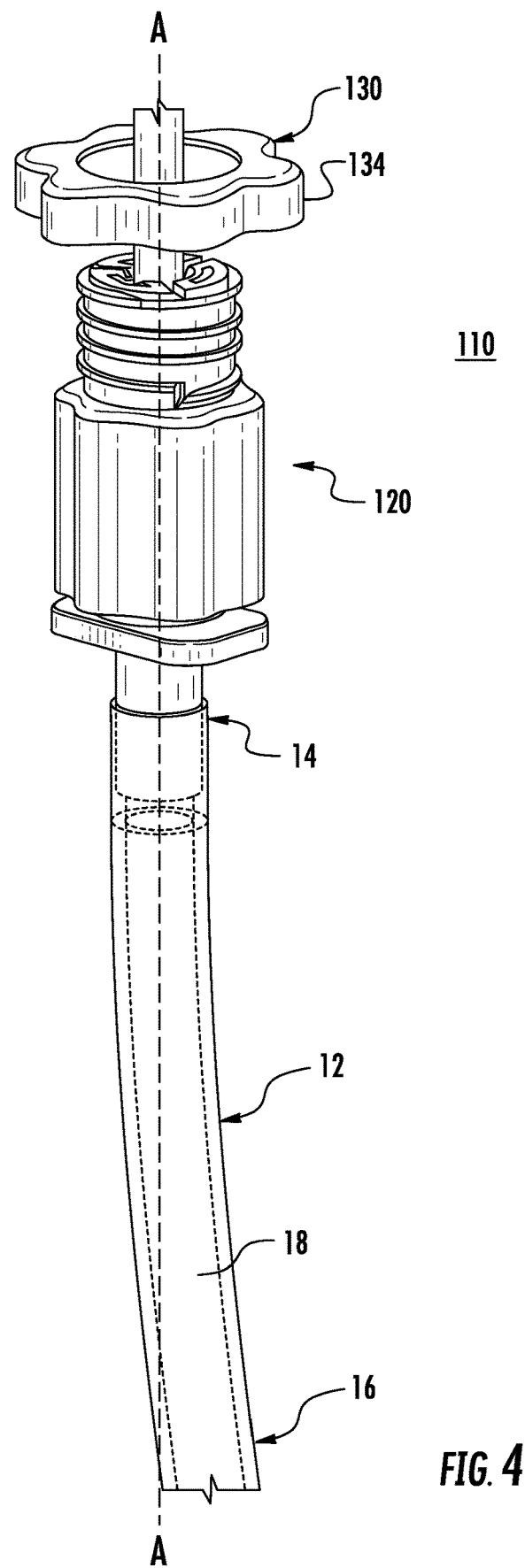
FIG. 4 is a perspective view of another tracheal tube assembly in accordance with the present disclosure with the channel in an uncompressed condition.

Referring to FIG. 4, another tracheal tube assembly 110 in accordance with the present disclosure is provided incorporating an elongated tube 12 and a locking mechanism 120.

Figure 5:
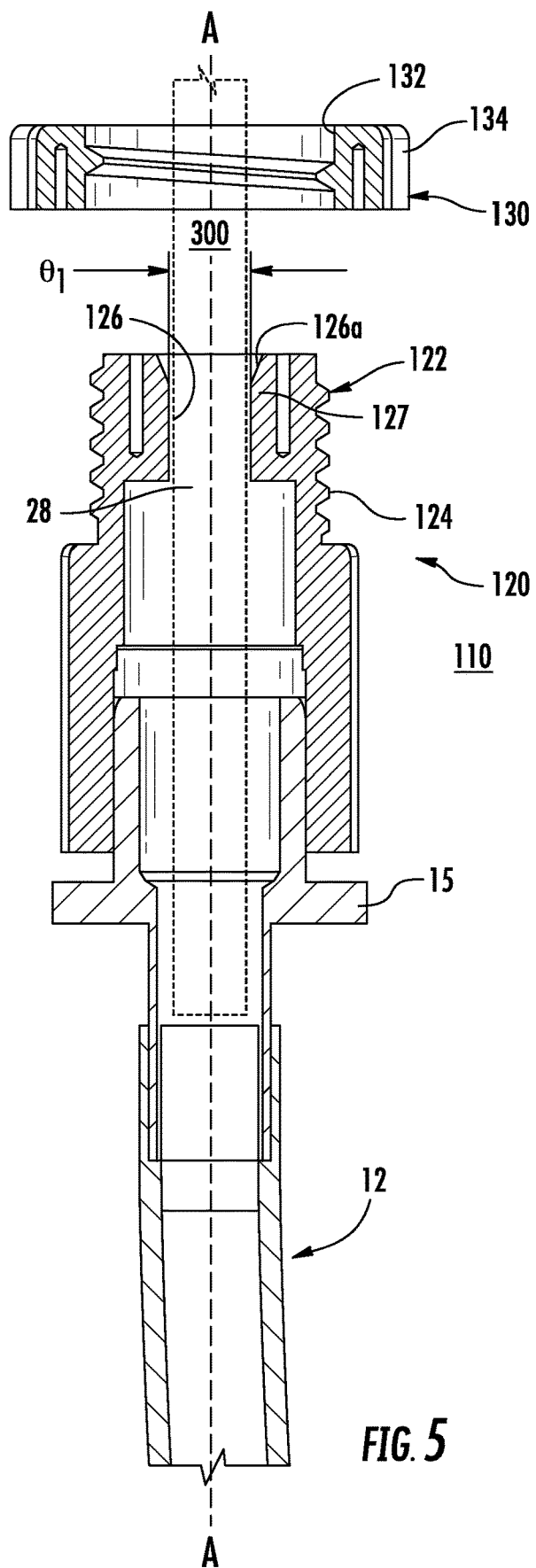
FIG. 5 is a cross-sectional view of the tracheal tube assembly of FIG. 4 taken along the longitudinal axis.
Figure 6:
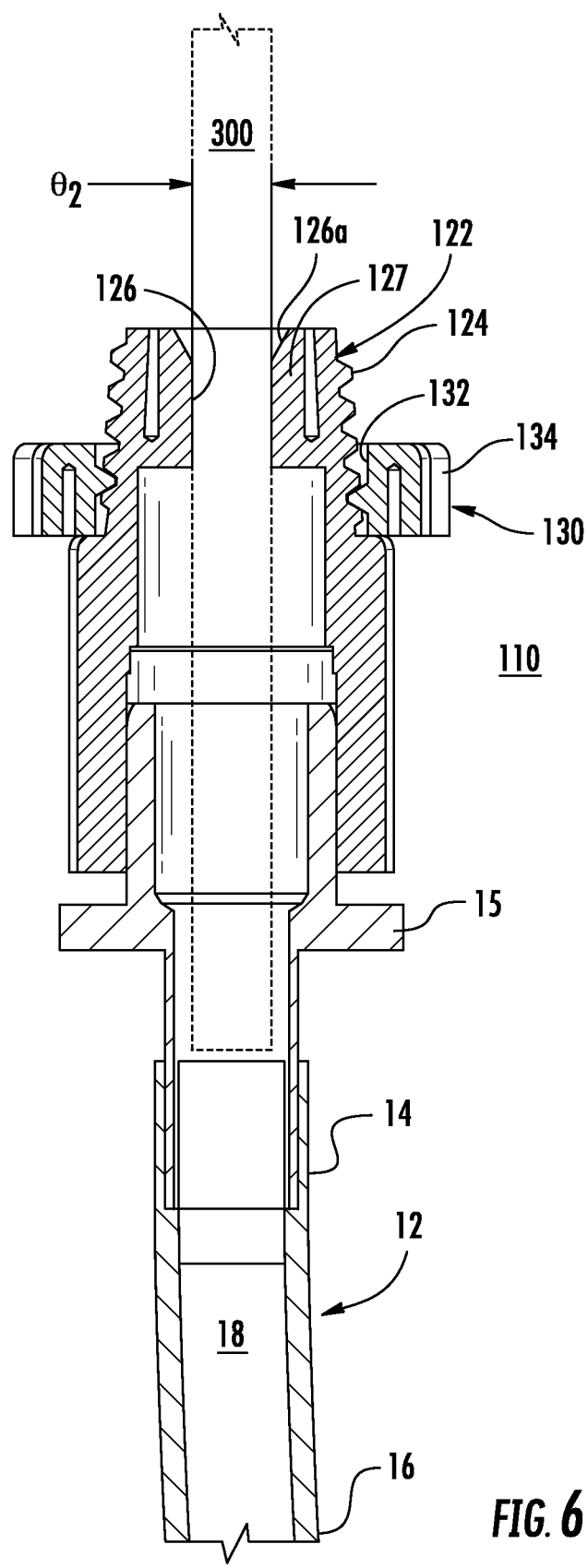
FIG. 6 is a cross-sectional view of the tracheal tube assembly of FIG. 4 taken along the longitudinal axis with the channel in a compressed condition.

With additional reference to FIGS. 5 and 6, the clamping member 122 includes a cantilevered member 127 coupled to a threaded portion 124. The cantilevered member 127 includes a clamping surface 126 configured to deflect as the clamping surface 126 engages the bronchoscope 300 positioned within the channel 28. The clamping surface 126 may be made of a soft compressible material configured to engage the surface of the bronchoscope 300. The deflection of the cantilevered member 127 maintains the clamping surface 126 substantially parallel to the longitudinal axis "A-A" allowing an increased length of the clamping surface 126 to engage the bronchoscope 300.

When the channel 28 is in the first position defining the first diameter $\theta_1$, a nut 130 of the locking mechanism 120 is positioned proximal to the threaded portion 124 of the clamping assembly 120. In some embodiments, the channel 28 is in the first position as the nut 130 engages the proximal end of the threaded portion 124. Similar to the nut 30 described above, when nut 130 is advanced over the threaded portion 124, the channel 28 is compressed achieving the second position defining a second diameter $\theta_2$ that is smaller than the first diameter $\theta_1$.

Figure 7:
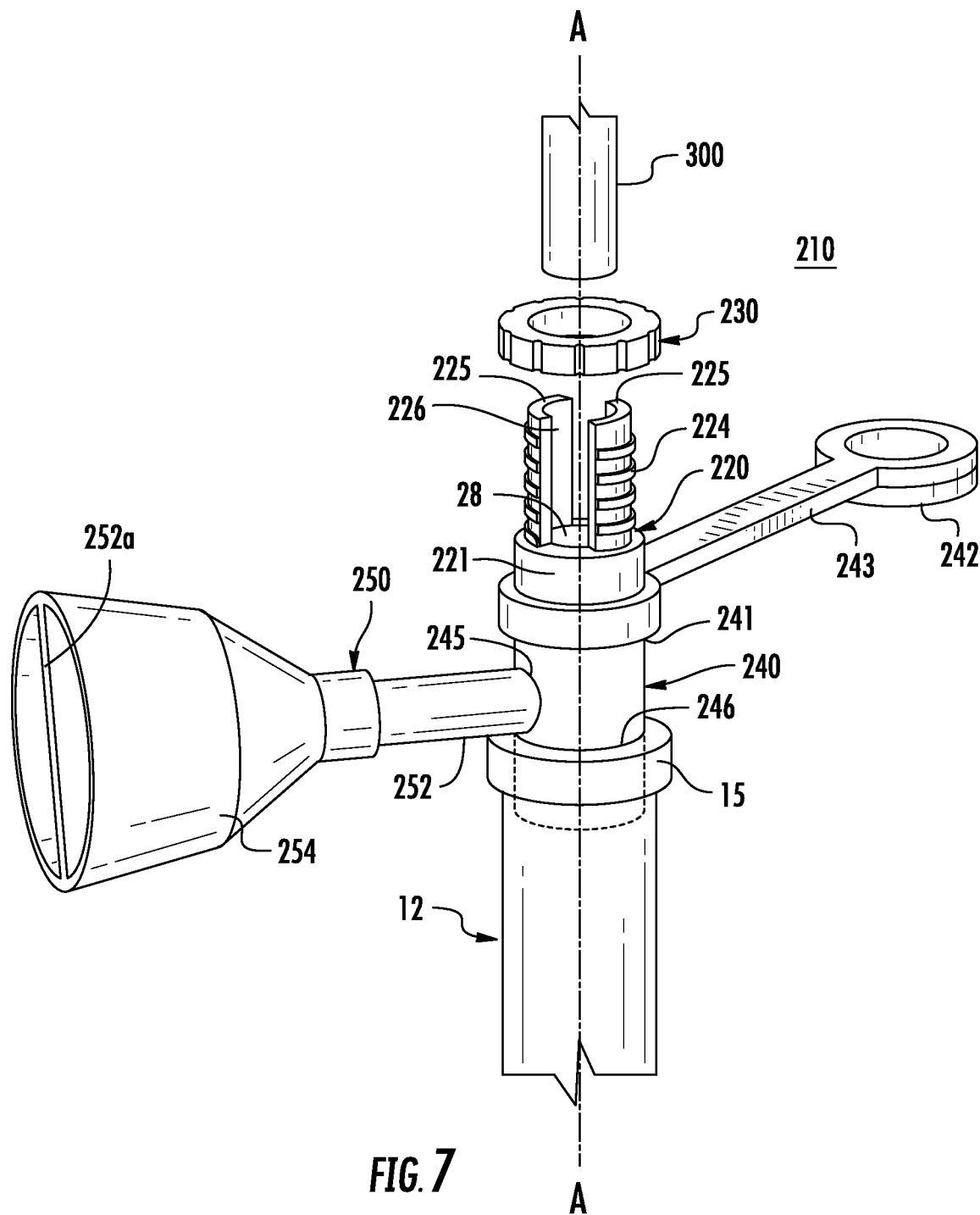
FIG. 7 is a perspective view of another tracheal tube assembly in accordance with the present disclosure with the channel in an uncompressed condition.
Figure 8:
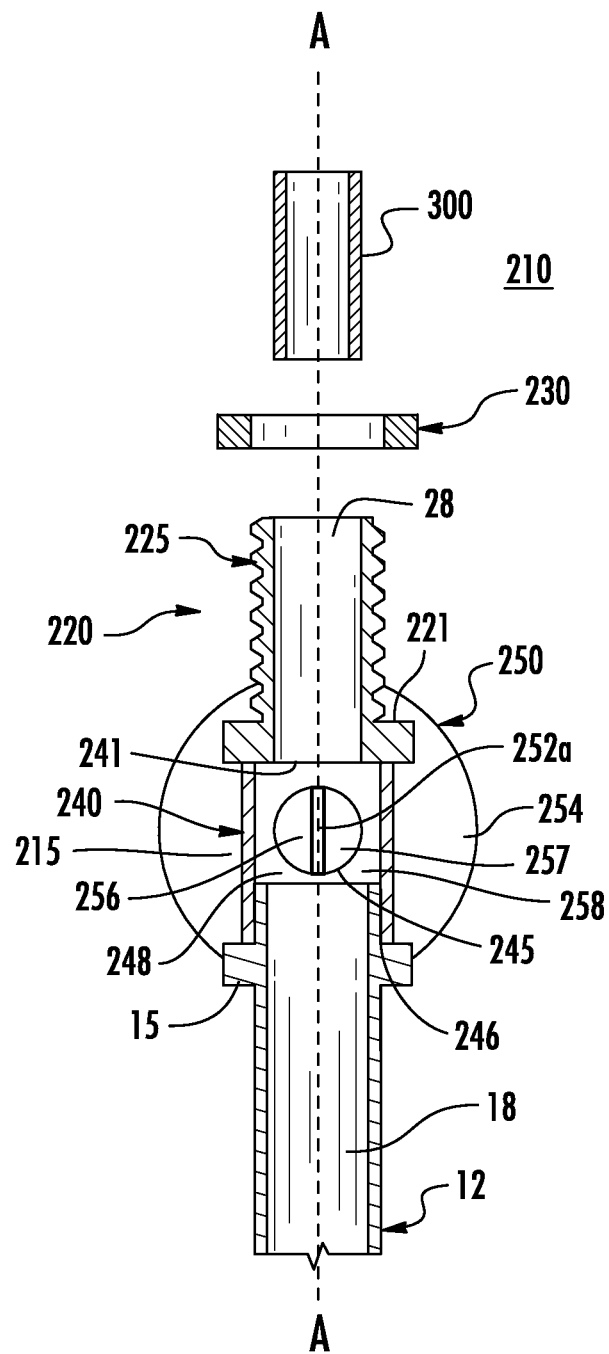
FIG. 8 is a cross-sectional view of the tracheal tube assembly of FIG. 7 taken along the longitudinal axis "A-A" as shown in FIG. 7.

Referring to FIGS. 7 and 8, another tracheal tube adapter assembly 210 in accordance with the present disclosure is provided incorporating a locking mechanism 220, an elbow portion 240, an airway connector 250, and an elongated tube 12. The elongate tube 12 may alternatively include a female connector (not shown) to allow connection to a male connector (not shown) of an airway device. For example, the female connector may be a 15 mm connector in accordance with ISO 5361 to allow connection to a 15 mm male connector.

The clamping member of the locking mechanism 220 is formed from two or more lobes 225 radially spaced about the longitudinal axis "A-A" with each lobe 225 including a portion of the clamping surface 226 and the threaded portion 224. As the nut 230 is advanced over the lobes 225, the space between each lobe 225 is reduced from a first diameter $\theta_1$ to a second diameter $\theta_2$ smaller than the first diameter $\theta_1$.

The elbow 240 includes an open proximal end 241, an open distal end 246, a sidewall opening 245, and a first passage 248. The locking mechanism 220 is coupled to the proximal end 241 of the elbow 240. The sidewall opening 245 is substantially orthogonal to the longitudinal axis "A-A" and is configured to receive the airway connector 250. Additionally or alternatively, the elbow 240 may be substantially "Y" shaped such that an acute angle is defined between the locking mechanism 220 and the airway connector 250. The first passage 248 is in communication with the channel 28.

A cap 242 having an arm 243 can be coupled near the proximal end of the elbow 240. The arm 243 extends away from the longitudinal axis "A-A" and is configured to fold to allow the cap 242 to seal the channel 28. In embodiments, the locking mechanism 220 includes a base 221 positioned distal of the threaded portion 224 of the lobes 225 and the cap 242 has an extended body 243, the cap 242 is configured to extend over the threaded portion 224 of the locking mechanism 220 to form a seal with the base 221.

The airway connector 250 is configured to provide ventilation through the elongated tube 12. The airway connector 250 includes an elongated body 252, a first coupler 254, and defines a first lumen 256. The first lumen 256 is disposed within the elongated body 252. In embodiments, the airway connector 250 can further include a second lumen 257 disposed within the elongated body 252. As shown in FIG. 8, the second lumen 257 is adjacent to the first lumen 256 with a septum 252a positioned between the first and second lumens 256, 257. In some embodiments, the second lumen 257 is disposed coaxially with the first lumen 256. The first coupler 254 can be a 15 mm connector configured to couple a breathing circuit or ventilator. Each lumen 256, 257 can include a directional valve (not shown) configure to inhibit fluid from flowing in one direction. For example, the first lumen 256 can include a valve (not shown) configured to permit fluid to flow from the first coupler 254 to the first passage 248 and inhibit fluid from flowing from the first passage 248 to the first coupler 254 and the second lumen 257 can include a valve (not shown) configured to permit fluid to flow from the first passage 248 to the first couple 254 and inhibit fluid from flowing from the first coupler 254 to the first passage 248.

The connector 15 defines a portion of lumen 18. The proximal end of the connector 15 is disposed over the distal end 246 of the elbow 240 with the lumen 18 in fluid communication with the first passage 248 and the channel 228. In embodiments, the lumen 18 has a diameter larger than the first passage 248. In some embodiments, the first passage 248 or lumen 18 forms a plenum in fluid communication with the first and second lumens 256, 257. In some embodiments, the first and second lumens 256, 257 extend through the sidewall opening 245 and the connector 15. The distal end of connector 15 is coupled in fluid communication to the proximal portion 14 of the elongated tube 12.

It will be appreciated that various components of the tracheal tube adapter assembly 210 may be rotatable relative to one another to reduce the likelihood of inadvertent decoupling of the components and to maintain air tight connections between the components. For example, the locking mechanism 220 may be rotatably relative to the elbow 240 and the airway connector 250 may be rotatable relative to the elbow 240. Rotation of the elements may minimize rotational or torsional forces between the components According to aspects of the present disclosure, a method for securing a bronchoscope includes inserting a bronchoscope into a channel of a locking mechanism and securing the bronchoscope by advancing a nut over a threaded portion of the locking mechanism. Any of the above tracheal adaptor assemblies 10, 110, and 210 can be used in conjunction with the method. The method may include inserting an instrument through the bronchoscope after the bronchoscope is secured in the locking mechanism. The instruments may include but are not limited to diagnostic (e.g., biopsy tools) and therapeutic (e.g., laser, cryogenic, radio frequency, or microwave tissue treatment probes) instruments.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A bronchoscope locking mechanism comprising:
 a clamping member including:
   an outer threaded portion; and
   an inner cantilevered member spaced radially inward of the threaded portion to define an annular gap between the threaded portion and the inner cantilevered member, the inner cantilevered member configured to flex relative to the threaded portion and including a clamping surface, the clamping surface defining a compressible channel, the compressible channel having a proximal segment and a distal segment, the distal segment configured for communication with a tracheal tube, the clamping surface including an angled guide configured to urge a bronchoscope into the compressible channel; and
 a nut having an inner threaded surface and an outer surface, the inner threaded surface configured to cooperate with an outer threaded surface of the threaded portion of the clamping member, wherein as the nut is advanced over the threaded portion, the nut interferes with the clamping member such that the compressible channel radially constricts about the bronchoscope to longitudinally fix the bronchoscope relative to the locking mechanism.

2. The locking mechanism of claim 1, wherein the outer surface of the nut is configured to enhance tactile feel.

3. The locking mechanism of claim 2, wherein the outer surface of the nut includes at least one of rounded protrusions, petal-shaped protrusions, star-shaped protrusions, wings, or knurling.

4. The locking mechanism of claim 1, further comprising a connector having a proximal section and a distal section, wherein the distal segment of the compressible channel is secured about the proximal section of the connector and the distal section of the connector is configured to be received within the tracheal tube.

5. A bronchoscope locking mechanism, comprising:
 a clamping member including:
   a threaded portion; and
   an inner cantilevered member spaced radially inward of the threaded portion to define an annular gap between the threaded portion and the inner cantilevered member, the inner cantilevered member configured to flex relative to the threaded portion and including a clamping surface defining a compressible channel, the clamping surface including an angled guide configured to urge a bronchoscope into the compressible channel; and
 a nut engaged with the clamping member and configured to be advanced thereover, wherein as the nut is advanced over the clamping member, the nut interferes with the clamping member such that the compressible channel longitudinally fixes the bronchoscope received within the compressible channel relative to the locking mechanism.

6. The locking mechanism of claim 5, wherein the nut includes an inner threaded surface and an outer surface, the inner threaded surface configured to threadingly engage an outer threaded surface of the threaded portion of the clamping member to advance the nut over the clamping member.

7. The locking mechanism of claim 5, wherein the angled guide extends circumferentially about a proximal end of the compressible channel.

8. The locking mechanism of claim 5, wherein an outer surface of the nut is configured to enhance tactile feel.

9. The locking mechanism of claim 5, further comprising a connector having a proximal section and a distal section, wherein a distal portion of the compressible channel is secured about the proximal section of the connector and the distal section of the connector is configured to be received within a tracheal tube.

10. A bronchoscope locking mechanism, comprising:
a clamping member including:
  a threaded portion; and
  an inner cantilevered member spaced radially inward of the threaded portion to define an annular gap between the threaded portion and the inner cantilevered member, the inner cantilevered member configured to flex relative to the threaded portion and including a clamping surface, the clamping surface defining a compressible channel, the clamping surface including an angled guide configured to urge a bronchoscope into the compressible channel; and
a nut having an inner threaded surface and an outer surface, the inner threaded surface configured to threadingly engage a threaded outer surface of the threaded portion of the clamping member,
wherein as the nut is advanced over the threaded portion, the nut interferes with the clamping member such that the compressible channel clamps a bronchoscope therein and longitudinally fixes the bronchoscope relative to the locking mechanism.

11. The locking mechanism of claim 10, wherein the compressible channel includes a proximal segment and a distal segment, the distal segment configured for communication with a tracheal tube.

\* \* \* \* \*